(12) United States Patent
Vajta

(10) Patent No.: US 6,399,375 B2
(45) Date of Patent: *Jun. 4, 2002

(54) METHOD AND APPARATUS FOR CULTURING CELLS AND TISSUES

(75) Inventor: Gabor Vajta, Tjele (DK)

(73) Assignee: Demtek A/S, Aarhus (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,025

(22) PCT Filed: Jan. 8, 1997

(86) PCT No.: PCT/DK97/00001

§ 371 (c)(1),
(2), (4) Date: Jul. 15, 1999

(87) PCT Pub. No.: WO98/30676

PCT Pub. Date: Jul. 16, 1998

(51) Int. Cl.[7] .............................. C12N 5/00; C12N 5/02
(52) U.S. Cl. .................. 435/374; 435/383; 435/325
(58) Field of Search ................................. 435/240, 374, 435/285, 383, 241, 286, 29, 325

(56) References Cited

U.S. PATENT DOCUMENTS 4,339,537 A * 7/1982 Sogi et al. ................. 435/240
5,312,630 A 5/1994 Pfaff ........................... 426/46

FOREIGN PATENT DOCUMENTS

WO    WO8501514    4/1985 ............ C12M/3/04

OTHER PUBLICATIONS

Fisher Scientific Catalog ; p.94, Water Baths, 1988.*

* cited by examiner

Primary Examiner—Jon P. Weber
Assistant Examiner—Patricia Patten
(74) Attorney, Agent, or Firm—Ladas & Parry

(57) ABSTRACT

Cells and tissues, in particular sensitive cells and tissues, such as oocytes, fertilized oocytes and preimplantation embryos, which require highly stable physical and chemical environment for in vitro development, are cultured in closed containers submerged or immersed in thermostatically controlled liquid baths, the containers being provided with an appropriate inner atmosphere containing, e.g. carbondioxide, oxygen and humidity in appropriate levels. The incubator containers may e.g. be gas and liquid impervious, flexible, sealable, preferably transparent bags which after sealing are submerged or immersed directly in the thermostatically controlled liquid bath. The liquid in the bath is preferably water. An incubator for submerse or immerse culture of cells and tissues in the above manner is also described. Also a transportable liquid incubator for culturing cells and tissues in the field is described.

14 Claims, 11 Drawing Sheets

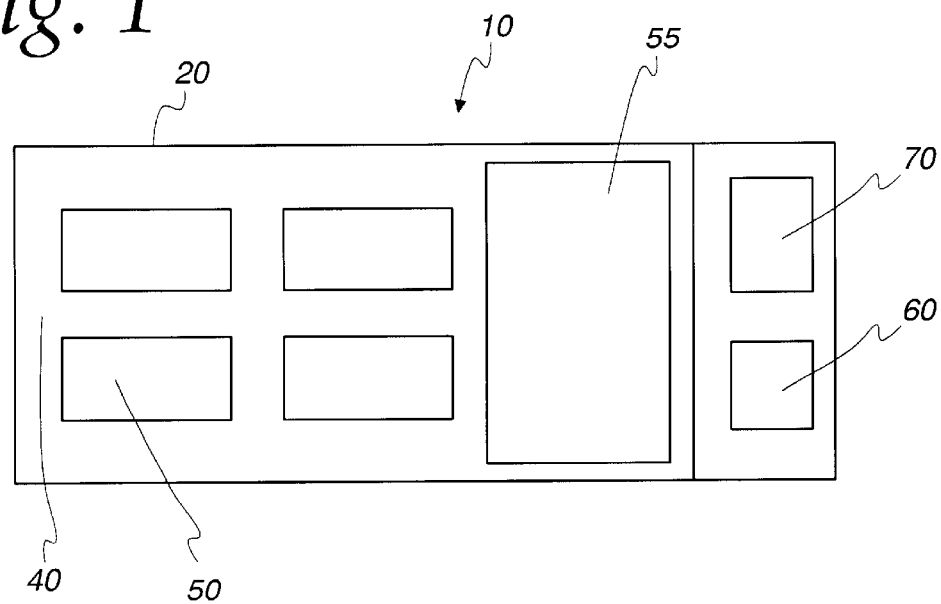
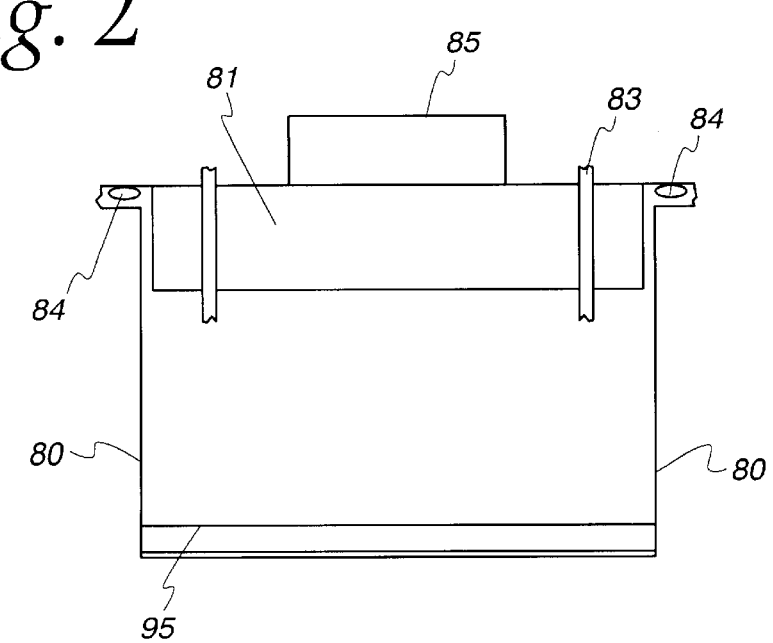

*Fig. 3* *Fig. 4*
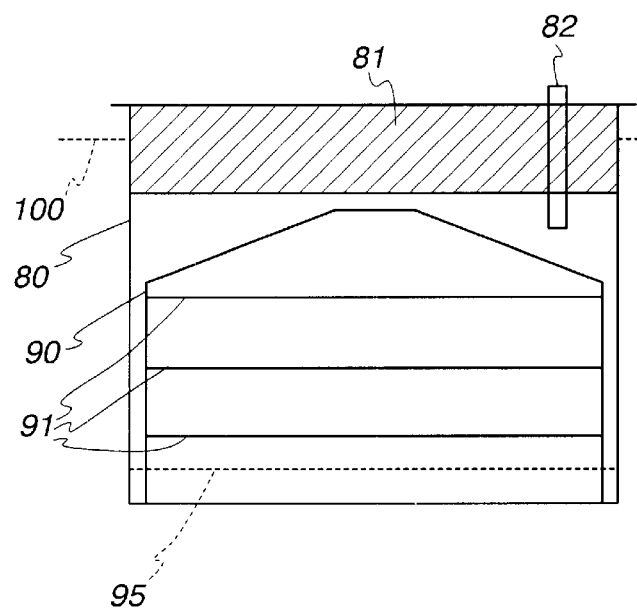
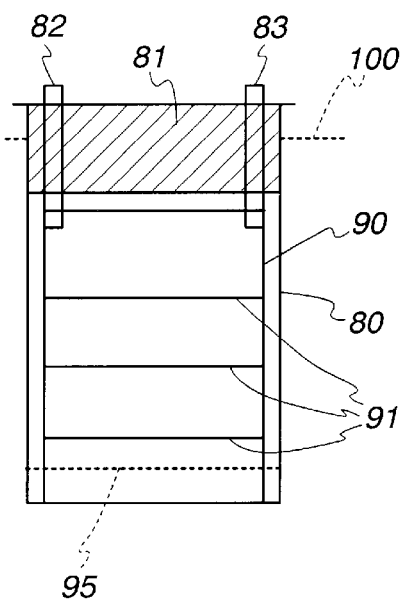

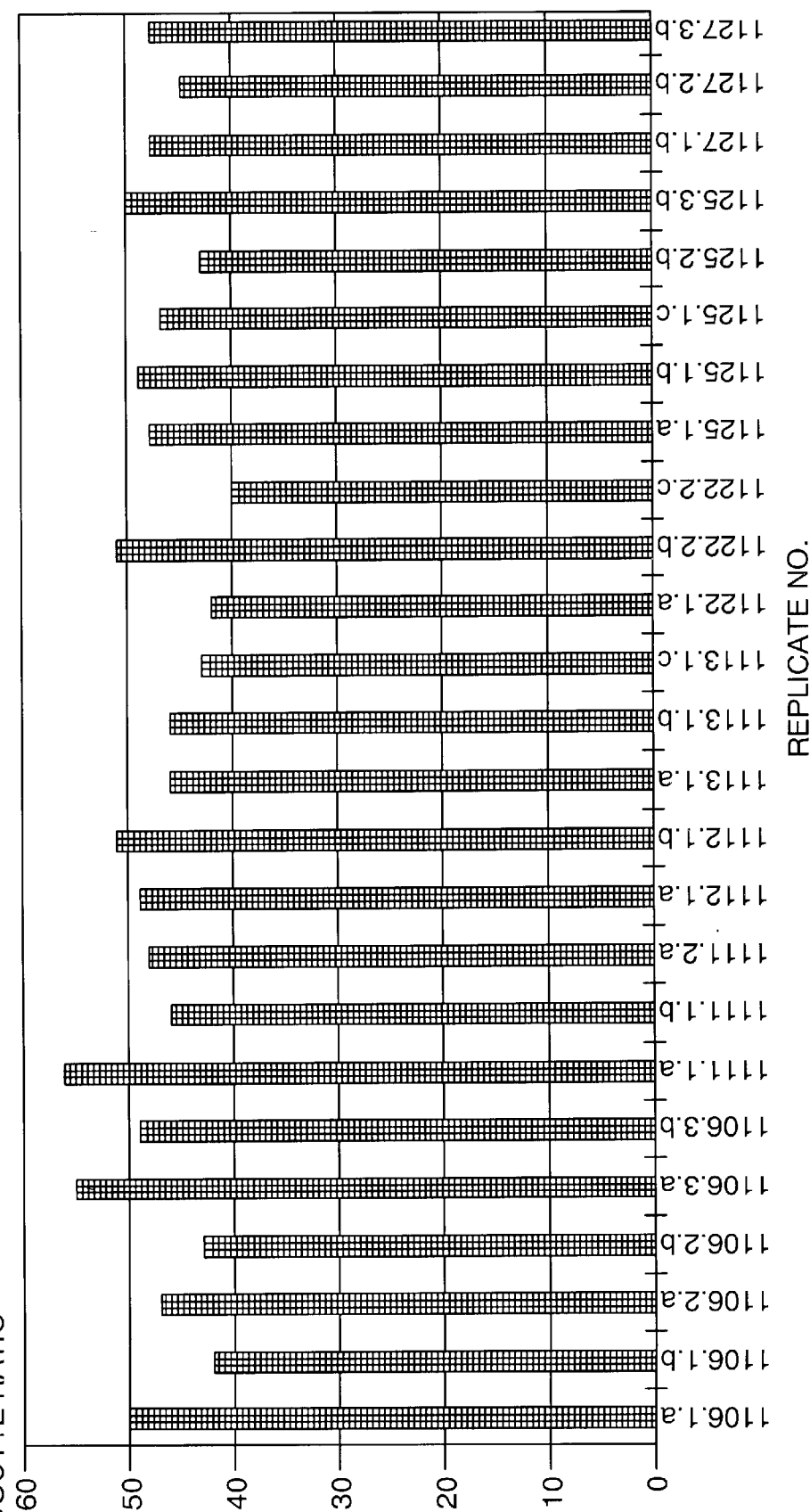
Fig. 14 PILOT EXPERIMENT 4.b: RESULTS OF 25 EMBRYO CULTURE EXPERIMENTS PERFORMED IN EXPIRATION AIR

METHOD AND APPARATUS FOR CULTURING CELLS AND TISSUES

INTRODUCTION

The present invention relates to a method and an apparatus for cultivation of cells and tissues. In particular the invention relates to in vitro cultivation, e.g. maturation, fertilization, growing, propagation, production and/or maintenance of cells and tissues, especially sensitive cells and tissues such as e.g. oocytes and embryos and other sensitive cells and tissues derived from multicellular organisms as well as certain sensitive bacteria, yeasts, fungi, molds and mucors which can advantageously be produced or propagated by the method and the apparatus of the present invention. Besides, genetically modified cells and tissues of the above origin, in particular such stemming from multicellular organisms like mammals and other warm-blooded animals, can be cultured by the method and apparatus of the present invention. Furthermore, the use of such cells and tissues for producing particular desired compounds and materials can also be effected by the method and apparatus of the present invention.

DESCRIPTION OF THE PRIOR ART

In vitro culture, e.g. maturation, fertilization, growth, propagation, production and/or maintenance, of certain sensitive cells and tissues, in particular such stemming from multicellular organisms like oocytes and preimplantation embryos, but also certain bacteria, yeasts, fungi, molds and mucors, and genetically modified cells and tissues, in particular cells and tissues stemming from multicellular organisms like mammals and other warm-blooded animals, require highly stable and constant environments in order to be successful.

Thus, the culture medium must contain at least water, salts, nutrients, essential amino acids, vitamins, hormones and possibly proteins and growth factors in well defined proportions and levels as well as a buffer system establishing a strict defined narrow pH-range and a source of oxygen.

Usually, the buffer system is a $CO_2$/bicarbonate buffer system, the bicarbonate being incorporated into the aqueous culture medium as from the start of the culturing period but may optionally be supplemented during the culture period from time to time, whereas the $CO_2$ (carbon dioxide) is provided from the atmosphere surrounding the culture medium during the culture period. The source of oxygen is usually gaseous free oxygen ($O_2$) which is also supplied from the surrounding atmosphere to the culture medium. Besides, the culture temperature should be kept within rather narrow limits in order to obtain optimum and/or successful results.

Small scale in vitro production, i.e. maturation, fertilization, growth, propagation etc. as mentioned above, of sensitive cells and tissues is usually effected in receptacles like small culture flasks, petri- or well-dishes provided with the culture medium and the necessary initial cells or tissues. The receptacles are then placed in an incubator which provide for a selected constant temperature and an environing atmosphere containing the gases necessary for development and/or maintenance of the particular cells or tissues concerned. In particular the necessary gases comprise humidity (i.e. water vapor), free oxygen ($O_2$) and carbon dioxide ($CO_2$) in specific proportions and levels.

Up to now the incubators used for the above production purposes have been provided in the form of cases or cabinets provided with insulating thermostate jackets, optionally one or more shelves for supporting the culture receptacles and dividing partially the interior volume of the incubator in two or more compartments, a (usually) vertically hinged front door providing access to the interior of the incubator, and one or more inlets and outlets for the gas or gas mixture to be supplied to and released from (respectively) the interior of the incubator. Such incubators may have a work space, i.e. an interior volume, of from as small as about 30–50 liters (except for some special types mentioned below) to as high as about 350 liters and even more and may be provided with sensors and control equipments for maintaining the temperature, humidity, carbon dioxide, oxygen and nitrogen at preselected levels in the interior of the incubator. The insulating thermostate jacket may be filled with water in order to provide easy and even delivery of heat to all points of the walls of the incubator and to avoid the risk of overheating which can be very harmful to the cell cultures in the incubator.

However, each time the front door of the incubator is opened during a working-day in order to inspect or remove a culture receptacle already placed in the incubator or to place a new culture receptacle in the incubator, all the parameters, i.a. the above mentioned, of the interior of the incubator and of all the culture receptacles therein are disturbed. The sensors and control equipments may restore the parameters in the interior volume of the incubators at the preset levels within about 10 minutes or so, but in the culture receptacles and media the restoration of the preselected levels of the parameters concerned may take much longer time. Furthermore, in as much as the front door of the incubator may be opened and closed many times during a working-day the cumulative effect on the development, growth and propagation of the cultured cells and tissues in the culture receptacles may be rather significant and serious, i.a. result in decreasing development and viability of the cells.

In particular mammalian oocytes and preimplantation embryos are considered to be very sensitive to environmental changes. On the other hand, in vitro production and propagation of such embryos requires frequent openings of the incubator door for changing or supplementing the culture media and transferring embryos from one culture receptacle to another. Professional laboratories working with in vitro production of embryos start up at least one in vitro fertilization program per day and try to avoid the above problems by purchasing a number of expensive $CO_2$ incubators and/or regulating the number and duration of openings per day of each incubator strictly and/or try to keep the temperature of the whole laboratory containing the incubators at a level as near as possible to that of the interior of the incubators, i.e. at about 37–39° C. However, the above approach does not solve all the technical problems concerned and from an economical point of view it is a very costly approach which is hard to realize for most laboratories.

Minimizing the size of the incubators, in particular their interior working spaces, might be beneficial to embryo development and has been studied by Boone and Saphiro, 1990; Avery and Greve, 1992; and Gordon, 1994. Analyzing the possible factors affecting embryo development, Avery and Greve (1992) found no direct correlation between negative effects on embryo development and frequency of door openings of large volume incubators and therefore supposed other factors to be involved, i.e. toxic fumes in the laboratory air or toxic components originating from the inner cupper walls of the incubator. However, later observations made by the present inventor (Vajta, 1994) after a series of unsuccessful embryo culture experiments in the same type of incubator, but with inner stainless steel walls instead of copper walls, revealed that high temperature differences could occur in the partially divided inner space of large incubators and could persist for hours after frequent openings of doors.

Some researchers therefore prefer working with culture receptacle(s) containing culture medium/media and placed in commercially available airtight plastic boxes, for example "modular incubator chambers" manufactured by Flow Laboratories (circular shape, 30 cm in diameter×12 cm in depth), which are placed in the incubator after filling or refilling them with the desired gas mixture. However, this requires a more complicated preparation procedure and the results obtained may vary. The plastic boxes may eliminate small temperature differences caused by frequent opening of the incubator door, but the cumulative effects may even be enhanced.

Small size double wall stainless steel boxes heated by warm water circulating in the space between the double wall construction provide a better solution of the above problems. Such boxes are commercially available from Henning Knudsen, Hillerød, Denmark, as K-system boxes. The size, stability and high recovery rate of gas and temperature levels render these boxes good candidates for embryo production (Avery and Greve, 1992). However, the high price of these K-system boxes prohibit most laboratories from purchasing the necessary optimum quantity of these boxes, i.e. at least one for maturation and fertilization experiment initiated and at least one for each continuing experiment. Moreover, even though the boxes are supplied with pre-mixed gas at a constant flow rate, recovery rate of the required atmospheric gas composition is still low and this problem is only partially solved by the possible manual increase of the flow rate of the gas mixture.

Single wall K-system boxes are less expensive, but require precisely heated environment. Placing these boxes in conventional incubators was up to now the best approach of producing embryos in an economical manner. However, as heat is transferred to the boxes by air-conduction, temperature recovery rates are not optimum and opening of the door of the incubator for working with one culture will disturb the physical parameters and environments of all the others in the incubator. Moreover, a single wall box requires a system to establish the correct gas mixture in each box in the incubator if optimum conditions shall be maintained within the boxes, which means high expenses for gas mixture consumption, control and regulating equipments and provides a source of complications, errors and troubles.

WO 85/01514 discloses a method and an apparatus for harvesting mammalian cells from an artificial substrate, which method comprises the step of exposing the cells to ultrasonic energy at a level which is sufficiently high to separate the cells from the substrate, but which is sufficiently low not to be harmful to the cells. The ultrasonic energy may be delivered to an external surface of a culture vessel, e.g. a roller flask dipped in a water bath having a temperature of approximately 37° C., containing the cells to be harvested. However, there is no disclosure or even a contemplation of culturing or growing the cells in a vessel immersed or submerged in the water bath before harvesting the cells.

U.S. Pat. No. 5,312,630 discloses a method and an apparatus for preparing an aerobically cultured plant material, such as a soyfood substrate, inoculated with a beneficial microorganism to form a cultured food, such as Tempeh. The culture is effected in trays which are supported on tray racks that are mounted in a water bath so that the trays are partially immersed in the water bath. The trays holding the inoculated soyfood substrate are sealed in the water bath by a cover which mount over the tray racks and is partially immersed in the water bath to seal the cover over and around the trays filled with the inoculated soyfood substrate. The cover can be a single, continuous member covering all the tray units in the water bath, or there can be individual covers, for each side-by-side tray unit. An aerating system provides for the aerobic culturing of the soyfood substrate while a circulating pump provides a uniform distribution of the water throughout the water tray. A sensor and a controller actuate a temperature control system to effect heating and cooling of the water bath as needed to promote the growth of the microorganisms on the soyfood substrate. However, this document does not suggest or contemplate the culturing of sensitive cells and/or tissues like e.g. oocytes and embryos requiring highly stable and constant environments both as to pH-range and composition of the culture medium as well as the composition of the environing atmosphere. Besides, the water bath is not sufficiently covered or sealed to secure an exact temperature control of the water in the water bath and thus neither in the culture trays.

Therefore, up to now no simple, reliable and inexpensive method of in vitro production of sensitive cells and tissues has been available, nor has any simple, reliable and inexpensive incubator system for such purpose. The present invention remedies these short-comings of the prior art.

DESCRIPTION OF THE INVENTION

Thus, the present inventor has discovered that excellent results can be obtained in the production of sensitive cells and tissues, specifically oocytes and preimplantation embryos, when the cells or tissues are cultured in containers, e.g. boxes, vessels or gasimpermeable bags, submerged or immersed in a thermostatically controlled liquid bath.

Hence, the present invention relates to a method of culturing cells and tissues in a container comprising a culture medium and a gaseous atmosphere, characterised in that said container is submerged or immersed in a thermostatically controlled liquid bath. In particular the cells and tissues cultured are sensitive cells and tissues.

In the present description and claims the words "submerged" or "submersed" are used synonymously and mean that the container (or any other object specifically mentioned in the context) is or has been placed at such depth in the liquid bath that a lower part of the container is below the upper level of the liquid in the bath, the outer surface of this lower part of the container being surrounded by and in contact with the liquid in the bath, whereas the remaining upper part of the container extends above the upper level of the liquid in the bath. Preferably, only the uppermost top-part of the container is above the upper surface of the liquid in liquid bath.

On the other hand the word "immersed" means in the present description and claims that the container (or any other object specifically mentioned in the context) is or has been placed at such depth of the liquid bath that all parts of the container are below the upper level of the liquid in the bath, the outer surface of the container being surrounded by and being in contact with the liquid in the bath, and no parts of the container extend above the upper surface of the liquid in the liquid bath.

The liquid of the liquid bath may be any suitable organic or inorganic liquid and should preferably be harmless. Examples of such liquids are mineral, synthetic, vegetable and animal oils, hydrocarbons, halogenated hydrocarbons, alcohols, esters, ethers and amides having a sufficiently high boiling point. A few examples of such liquids are glycerin, ethyleneglycol, ethylacetate, butylacetate, diethylcellusolve, dioxane, and diethyl- and dimethyl formamide. Preferably, however, the liquid is water or water mixed with another liquid or compound miscible with or soluble in water.

The liquid may comprise any suitable biocide or antibiotic, like e.g. a bacteriocide, fungicide, algaecide, acariacide or insecticide or a mixture thereof, in order to avoid contamination of the liquid bath with micro organisms or infectant organisms and thereby minimizing the risk of contamination of the interior of the culture containers and infection of the cultures contained therein.

The liquid bath should be well circulated, stirred or agitated so that the temperature of the bath is essentially the same throughout the liquid in the bath at any time. Besides, the temperature of the liquid should be carefully controlled and preferably be kept within a range of ±1° C. of the preselected level, more preferably within a range of ±0.5° C., yet more preferably within ±0.01° C., most preferably within ±0.05° C. or less. In fact commercially available thermostate controlled water baths are capable of maintaining the temperature of the water in the bath within a range of ±0.05° C. from the preselected level in the whole bath. This is a very important feature because one of the most essential factors for in vitro culture of embryos is simply to control the temperature at any time within the minimum and maximum of the in vivo occuring physiological levels. Another advantage of liquid heating is, that overheating, which occassionally occurs in air-heated systems, may be completely excluded.

In one embodiment of the method of the invention the culture of the cells and/or tissues is effected in a vessel submerged in the liquid bath and provided with a removable cover or lid secured airtight to said vessel at its top side. Preferably the said cover is of a heat insulating material and the container is submerged to such depth in the liquid bath that the top surface of the cover is above the upper level of the liquid bath and the lower surface of the cover is below the said level of the liquid bath. Preferably the cover is provided with at least one inlet for supplying a preheated gas mixture to the interior of the vessel and at least one outlet for releasing excess gas to the general surroundings. The inlet and outlet may be in the form of pipe stubs extending through the cover to or into the interior of the container and connected at the outside of the cover with valves and tubes or hoses. The inlet gas mixture may be preheated by being passed through a spiral tube immersed in the same liquid bath as the culture vessel before it enters into the culture vessel. Preferably such spiral tube is in the form of a thin-walled metal tube having good thermal conductivity. Also the culture container itself is preferably made of metal having satisfactory thermal conductivity, e.g. stainless steel. The cover of the culture container is preferably made of a non-translucent material when the cells and/or tissues to be cultured are sensitive to light radiation, but this will of course prevent direct inspection and observation of the cultured cells without removing the vessel from the bath or at least opening the vessel by removing or pivoting the cover of the vessel.

A semi-automatic mechanism for filling the vessels with gas may also be applied. Gas inlets and outlets may be equipped with a valve: the inlets are open when the gas tube is connected, while the outlets are open when the pressure inside is higher than outside. At filling the vessels with a preheated gas mixture, the tube carrying the gas should be connected to the gas inlet valve, and the flow of the gas mixture may be started by pressing the bottom of a time-regulated valve, which stops automatically after 2 to 4 minutes, when the box is completely filled with the gas mixture.

In its simplest form the culture medium containing the cells to be grown is just placed on the bottom of the vessel. However, in that case only one culture experiment can be effected at a time. Therefore, in a preferred embodiment the production of cells is effected in separate receptacles like culture flasks, petri- or well-dishes optionally enclosed in sealed bags of plastic film, metal foils or more preferably laminates of such materials. These receptacles may be placed on the bottom of the vessel or more expedient on the shelves of a rack which is placed in the vessel. In the latter case a water layer can be provided on the bottom of the container for maintaining sufficient humidity in the interior of the culture container.

It has been discovered that excellent results are obtained when culturing cells with the above embodiments of the method of the invention, apparently because it is possible to maintain the culture conditions, in particular the temperature and the composition of the surrounding atmosphere, stable and constant to an extent not obtainable hitherto by any other method or equipment. Besides, manipulation of one vessel does not at all affect the physical parameters and compositions of the environments of the other culture vessels in the same liquid bath. Finally, infections occasionally occurring in tissue cultures, especially at primary cultures as embryo culturing, cause minimal problems with LBI: removable boxes may be cleaned, sterilized without disturbing the function of the whole device.

In a further embodiment of the method of the invention the culture of cells and/or tissues is effected in a receptacle, e.g. a petri- or well-dish, containing a culture medium and enclosed in an airtight sealed flexible bag provided with an appropriate atmosphere, which bag is submerged or immersed directly in a thermostate controlled liquid bath. In this embodiment the bag is expediently placed in a foramenious, grid or wire mesh basket or a rack with grid or wire mesh shelves in order to lower the bag to the desired depth of the liquid bath. The baskets and racks may be made of metal or plastic.

The appropriate gas mixture is passed into the bag before sealing it or it can be passed into the bag after its sealing when the bag is provided with an inlet for supplying the desired gas or gas mixture and an outlet for releasing excess gas to the surroundings. The in- and outlet should be provided with valves or other appropriate means, e.g. clamp or stop cocks or hot sealing facilities, for closing the access to the bag hermetically. Alternatively, a presealed bag can be filled with the proper gas mixture through a sterile injection needle passed through the wall of the bag into its interior volume whereupon the needle is retracted and the puncture hole in the bag is sealed. The culture receptacle containing the cell(s) to be grown is in the former and latter cases always and in the middle case preferably introduced into the bag before sealing it.

The bag to be used is optionally manufactured of a transparent plastic film or laminate allowing inspection and observation of the cultured cells during the culture period without breaking the sealed bag and without or with only minimum disturbance of the cultured cells and their environmental conditions. However, the bags to be used may also be manufactured of a non-translucent film material, e.g. a plastic film laminate comprising a metal foil, e.g. of aluminium. Such bag are particular suitable for culturing light sensitive cells and tissues for prolonged periods of time.

If the culture medium and cells to be grown are placed in a receptacle like a well- or petri-dish which in turn is introduced into a transparent plastic film or laminate bag which is then sealed, a thin layer of a sterile liquid, preferably oil, could be used to keep the inner surface of the bag attached to the surface of the culture dish to increase optical clarity for direct microscopic examination. In this way direct observation and examination is possible at most magnifications. According to experiments performed by the inventor, a limited number (at least up to 5) of investigations and photographings does not decrease the development of embryos (see Pilot experiment 6). When a bag is placed on a preheated microscopic stage and covered with a transparent plastic or glas box to increase heat-stability, microscopic observation in this manner can be continued for extended periods of more than one week.

Besides, culturing sensitive cells and tissues, in particular mammalian oocytes and preimplantation embryos, in a culture medium introduced into a flexible bag provided with an appropriate environing gas mixture, which is then submerged or immersed in a thermostate controlled liquid bath, has proved to provide some quite unexpected advantages and possibilities.

Thus, if the culture of cells and/or tissues is effected in air-filled bags (i.e. containing the appropriate gas mixture) the system is uniquely suitable to perform experiments under limited pressure exactly defined by the depth of immersion of the bags into the liquid of the bath. Limited overpressure might have beneficial effects on development of certain tissues as well as embryos of certain species (see Pilot experiment 2a). On the other hand it has been proven that overpressure occurring at up to 9 centimeter water depth (from the surface) has no harmful effect on the development of bovine embryos (see Pilot experiment 2b).

Another particular advantage of this system is that the bags can be submerged or immersed for a limited period into a liquid of a temperature lower or higher than the physiological one, for example to activate enucleated oocytes at ±10° C. for cloning by nuclear transfer. A rapid and well controlled change of the temperature can then be obtained in a very simple way without disturbing the appropriate gas atmosphere surrounding the cultures, e.g. by transferring the bag to another liquid bath incubator having a different temperature or by suddenly changing the temperature of the liquid in the same liquid bath incubator. (For need of such temperature changes see P. Chesne et al., 1993).

Furthermore, as the flexible bags can be filled with an unlimited variety of gas mixtures, the system provides a very simple possibility for performing cell, tissue or embryo cultures in specifically composed gas mixture atmospheres or for making comparative experiments investigating the effect of different levels of certain components of the culture atmosphere. For bovine embryo maturation and fertilization, for example, a gas mixture consisting of 5% carbon dioxide in air is used by many laboratories worldwide. However, for embryo culture certain culture forms require a gas mixture consisting of 5% oxygen, 5% carbon dioxide and 90% nitrogen. Other cultures have to be performed in 5% carbon dioxide in air, 2% carbon dioxide in air, etc. (For need of such different culture atmospheres see Y. Fukui et al., 1991).—So far, no simple and inexpensive equipment offering the flexibility of the present invention in this field has been available.

Experiments performed completely in the sub- or immersed bag system have led to the discovery that the optimum composition of the surrounding atmosphere used in the system for culturing bovine embryos is lower in carbon dioxide content than the 5% carbon dioxide in air used previously. The percentage of oocytes developing to the blastocysts stage is significantly higher when the carbon dioxide level is lowered to 3,5% (see Pilot experiment 3).

The cultivation of the sensitive cells and tissues like oocytes and embryos in air-filled flexible bags has the further advantage that the initiation of the culture, i.e. initial growth of the cells, need not to be started in a laboratory having the necessary complicated and sophisticated laboratory equipments, but can be commenced on location in the field.

Thus, in addition to flexible sealable bags the only further equipment necessary for initiation of the maturation of oocytes removed from an animal on a farm in the country is just a relatively simple (preferably electrically) heated and temperature controlled thermos flask or container filled with a liquid, preferably water, of the appropriate temperature. Such thermos flask, bottle or container can be electrically powered from a battery, an accumulator or a car cigaret lighter plug. The necessary gas mixture to be loaded into a bag before sealing it after introduction of culture medium, oocyte(s) can simply be expiration air blown into the bag by a person, e.g. the researcher. Expiration air has a rather constant $CO_2$ level of about 4% (by volume) and an $O_2$ level of about 16% (by volume) and it has been established that cultivation of fertilized bovine oocytes can be performed in a period of at least seven days without need for breaking the sealed bag and replenish, modify or exchange neither the culture medium nor the environing atmosphere provided in this way, i.e. until the development of the blastocyst stage has occured. Comparing development of fertilized oocytes performed either in 4% carbon dioxide in air stemming from a compressed air bottle or expiration air, in a laboratory water bath incubator with high temperature stability disclosed no significant differences (see Pilot experiment 4). Experiments performed for the whole culture period (7 days) in a transportable thermos flask with slightly less accurate temperature stability resulted also in good blastocyst rates (see Pilot experiment 5).

The above embodiment of the invention allows not only embryology work to be initiated on location in the field, but also performance of culture of sensible cells and tissues nearly anywhere, e.g. in connection with sampling in the jungle, wilderness, desert or the arctic or antarctic areas of the Globe.

The present invention also comprises equipment for performing the method of the invention.

Thus, the invention also relates to an incubator for culturing cells and tissues, comprising a tank to be filled with a liquid, means for heating said liquid, means for controlling the temperature of the liquid so as to be maintained essentially constant at a selected level and means for circulating, stirring or agitating the liquid in the tank so that the temperature of the liquid is essentially the same throughout the liquid in the tank, said tank being provided with a roof (i.e. cover) having one or more openings for receiving each a container, basket or rack to be submerged or immersed in the liquid in the tank, and optionally a thermal insulating cover to close the opening after sub- or immersion of the container(s), basket(s) or rack(s) in the liquid. The tank should preferably be thermal insulated by an insulating jacket and the roof should preferably be made of a thermal insulating material.

The container to be sub- or immersed in the tank liquid can be a vessel provided with a lid secured airtight thereto and wherein at least one inlet is passed through the lid for supplyig a preheated gas mixture to the interior of the vessel and at least one outlet is passed through the lid for releasing excess gas to the surroundings. The inlet and outlet may be in the form of pipe stubs extending through the lid to or into the interior of the container and connected at the outside of the lid with valves and tubes or hoses. The inlet tube is connected to a heating means, preferably a tube immersed in the same liquid bath as the culture vessel so as to heat the entering gas mixture to essentially the same temperature as that of the liquid bath before it is passed into the culture vessel. Preferably such tube is in the form of a spiral shaped, thin-walled metal tube having good thermal conductivity. Also the culture vessel itself is preferably made of metal having satisfactory thermal conductivity, e.g. stainless steel. The lid of the culture vessel can be made of a transparent material so that inspection and observation of the cultured cells can be effected without removing the vessel from the bath and even without opening the vessel by removing or pivoting the lid of the vessel, but when the cells or tissues to be cultured are sensitive to light radiation the lid should be made of a non-translucent material or it should be covered with a layer or sheet of such material.

The vessel may have any suitable shape, e.g. box shaped, spherical or cylindrical shaped or supereliptical shaped, but is preferably box-shaped with rounded comers so as to facilitate cleaning of the vessel.

The lid of the vessel should be manufactured of a thermal insulating material and either be double-walled or be of a sufficient thickness. Preferably it is made of a plastic material.

Baskets or racks provided with shelves may be placed in the vessels for supporting separate culture receptacles like culture flasks, petri- or well-dishes or sealed bags containing the culture medium and the cells to be grown. Such baskets and racks can be manufactured of a plastic material or a metal, in particular stainless steel. The baskets and shelves are preferably made of wire mesh or gratings of the above materials.

The container to be sub- or immersed in the thermostate controlled liquid in the tank can also be in the form of an air-tight sealable flexible bag which is to enclose a receptacle filled with culture medium, the cells or the tissues to be grown and an appropriate gas or gas mixture and then sealed.

The inside of the bag may be provided with a film or a layer of a heat sealable material so that the bag can simply be hermetically closed by heat sealing a stripe across the bag near its open end. In case the bag is to be formed of a flexible film tube provided with an inner heat sealable film material, the tube will have to be cut into appropriate lengths, the ends of which will have to be heat sealed, usually first a bottom end and then a top end. The bag can also be manufactured of a sheet of such film material by cutting it into appropriate rectangular pieces which are then folded along a central line, heat sealed along the two side edges and finally at its top edge (after introduction of the culture receptacle). Alternatively, the bag can be manufactured of a laminate film sheet material having a heat sealable film layer adhered to one of its surfaces by cutting appropriate rectangular pieces of such material and placing two such rectangular pieces on top of each other, the heat sealable layers facing each other, and then effecting heat sealing along three of the edges of the whole assembly, the fourth remaining unsealed until use of the bag.

The flexible sealable bag may, however, also be provided with a pressure sensitive adhesive attached circumferentially along a stripe on the inside surface of the bag at or near its open end(s), which adhesive stripe is initially covered with a slip tape or strip which upon removal makes it possible to seal the bag air-tight by effecting a calendering pressure on the outside of the bag along the adhesive stripe area inside the bag.

The bag may be provided with an inlet for supplying the desired gas or gas mixture to the bag and an outlet for releasing excess gas to the surroundings. The in- and outlet may be in the form of pipe stubs provided with or connected to valves or other appropriate means, e.g. clamp or stop cocks or hot sealing facilities, for closing the accesses to the bag hermetically.

The bag should be made of a gas impermeable material and should also be impermeable to and insoluble in the liquid in the tank. Optionally the bag is manufactured of a transparent plastic film or laminate material allowing inspection and observation of the cultured cells enclosed in the bag. Films sold by Rexam Metallising under the trade name Camclear Polyester Laminate 12/45, Anti-Fog, have proved to be particular suitable. Dew gathering on the inside of bags made of this film material, which may prevent a clear view of cells or tissues enclosed in the bags, can be prevented by oiling the inner surface of the bags or by treating it with other suitable anti-fog or liquid means. However, a metal foil can be included in the laminate material in order to complete its impermeability to gas and liquid, but this will of course prevent direct visual observation of the cells enclosed in the bags.

The culture medium and cells to be grown may be introduced directly in the bag which is then sealed after introduction of the appropriate gas mixture. However, the culture medium and cells to be grown are preferably placed in receptacles like well- or petri-dishes which is then introduced into the bag, which is supplied with the appropriate gas mixture and then sealed.

Even though it is advantageous that the bag and the optional receptacles contained therein are transparent so as to make it possible to inspect and observe the cells and culture medium during the culture period it may be advantageous too to cover the opening in the roof of the tank after sub- or immersing the bag in the liquid in the tank with a non-translucent cover, because the cells, in particular oocytes and preimplantation embryos, are sensitive to light and other form of radiation.

The invention also comprises a transportable combination kit for performing cell and tissue culture on location in the field, said combination kit comprises a (electrically) heated and thermostate controlled thermos container, flask or bottle filled with an appropriate liquid, in particular water, and air-tight, flexible, sealable bags and optional culture receptacles like petri- and well-dishes. The thermos container, flask or bottle can be electrical powered from a battery, an accumulator or a car cigaret lighter plug. If optimum gas mixtures are not available under field conditions expiration air from the lungs of a person can be used instead.

The invention will now be described in further details with reference to the examples given below and the accompanying drawings, wherein:

FIG. 1 is a top view of an embodiment of a liquid bath incubator according to the present invention covered with a roof containing openings for submerging both vessels and basket(s) and/or rack(s) in the liquid in the incubator tank;

FIG. 2 is a sectional side view of a box-shaped vessel in the tank of the incubator shown in FIG. 1;

FIG. 3 is a sectional side view of a box-shaped vessel in the tank of the incubator shown in FIG. 1;

FIG. 4 is a sectional end view of the vessel shown in FIG. 3;

Figure 10:
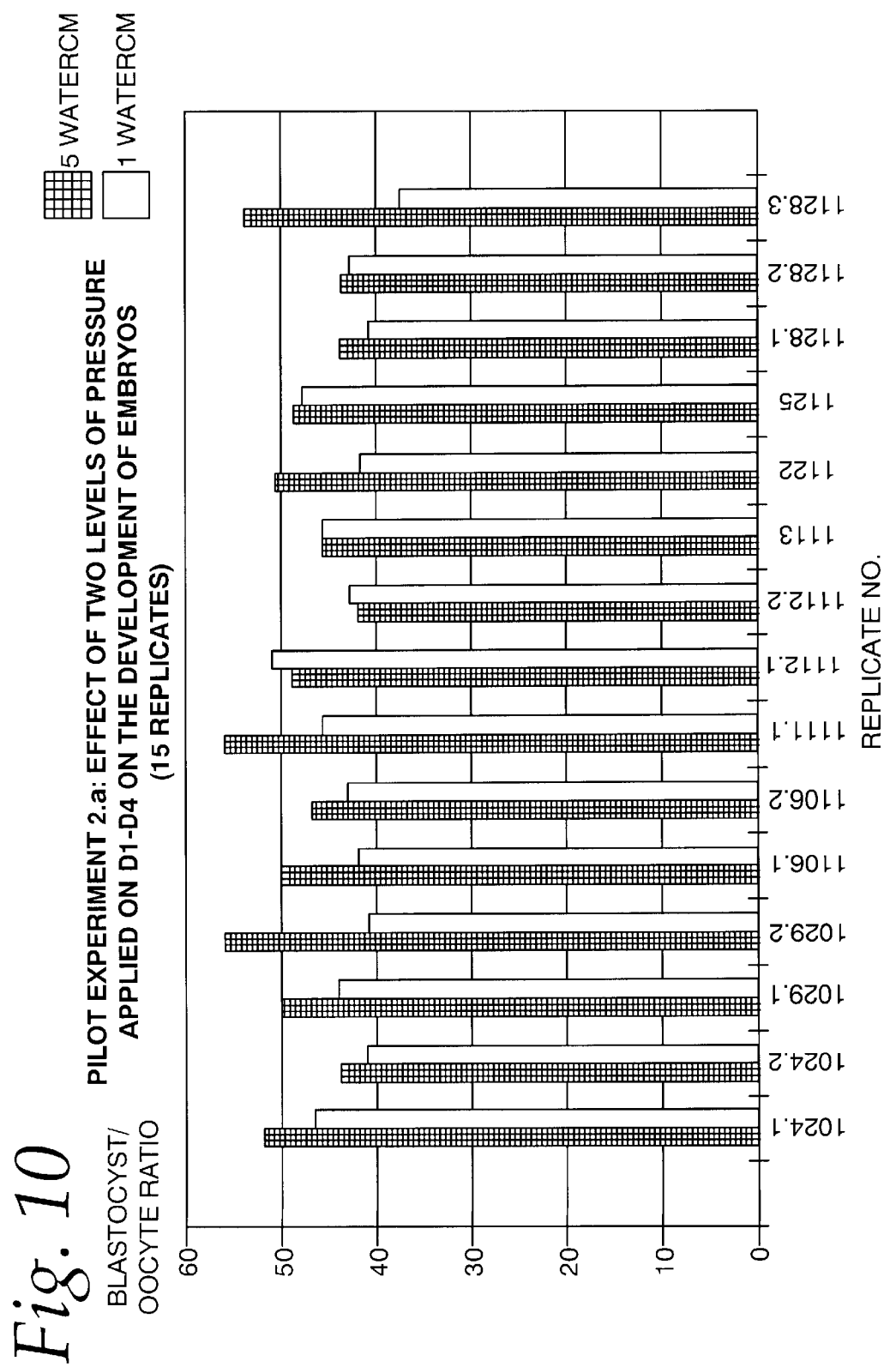
Figure 11:
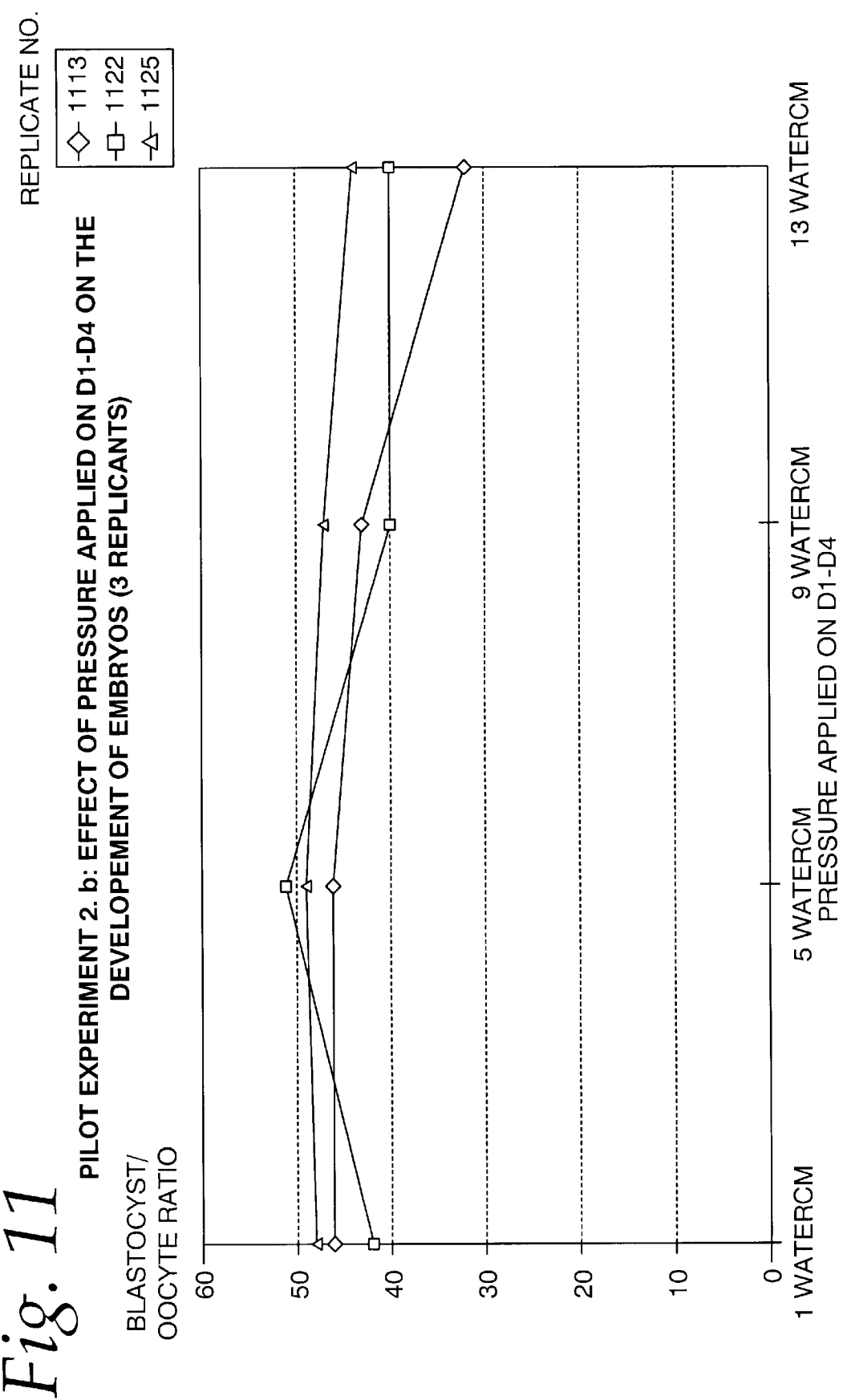
Figure 12:
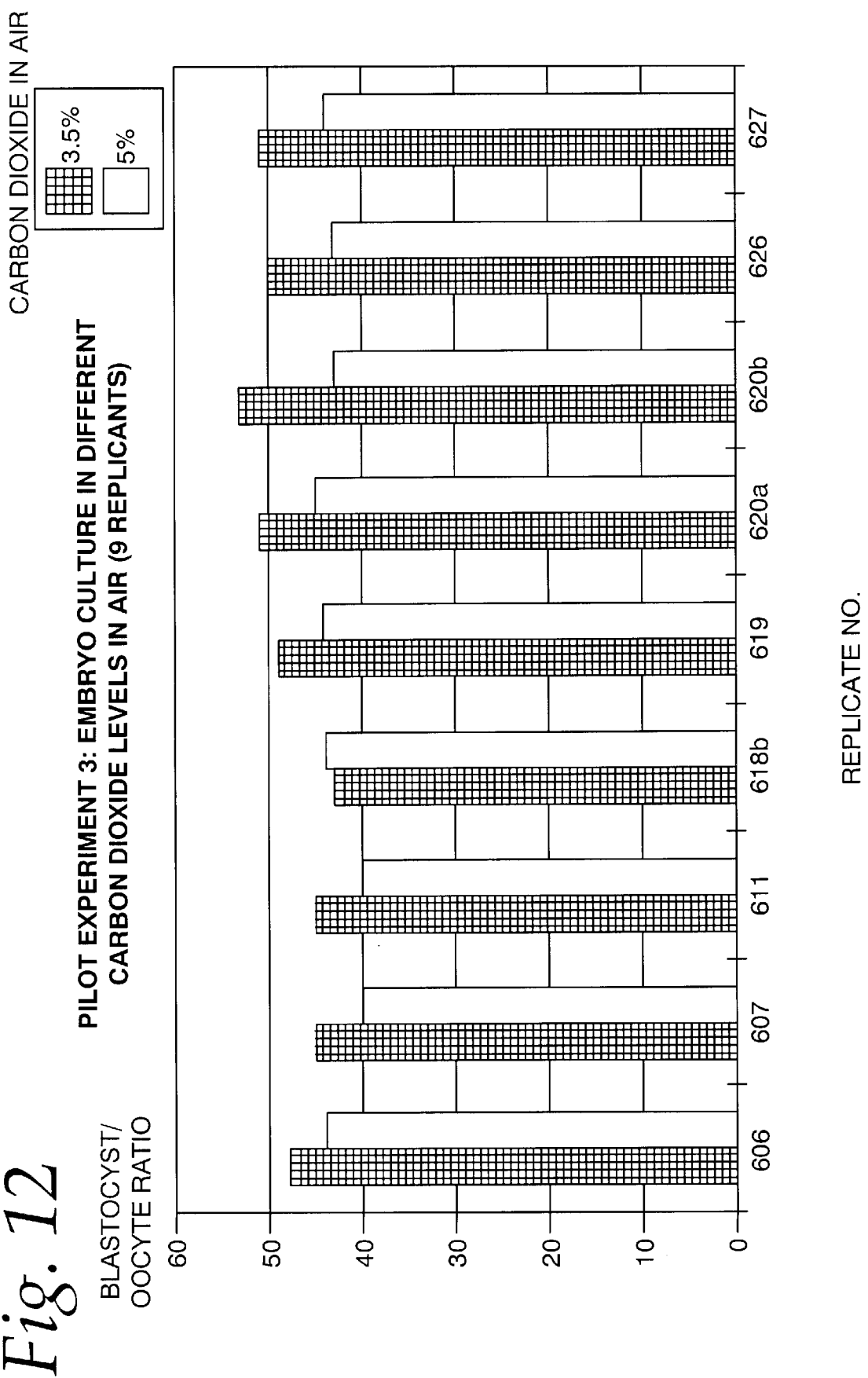
Figure 13:
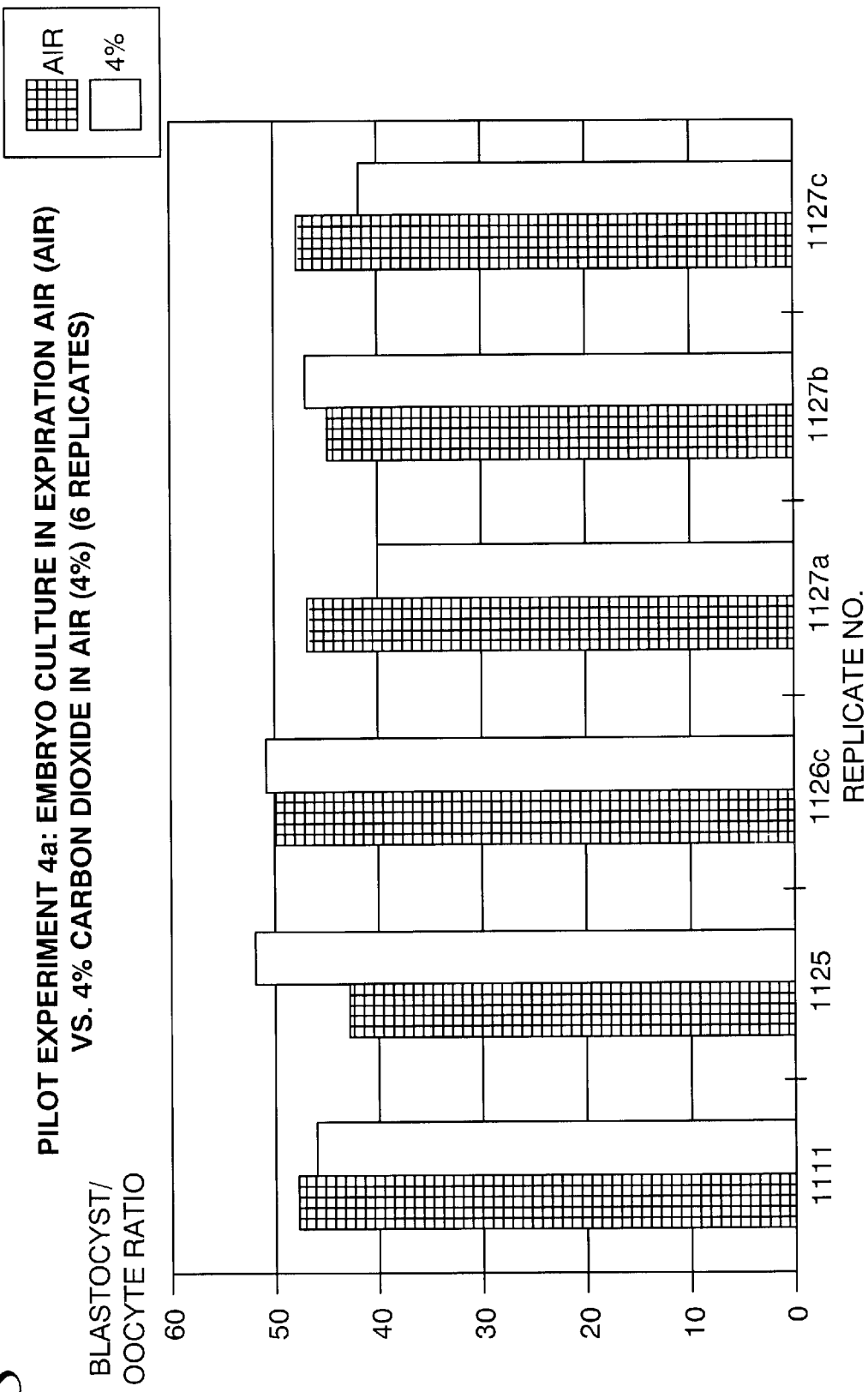

FIG. 10 is a bar chart showing the results of embryo development in air-tight flexible laminate foil bags filled with expiration air and immersed to either 1 cm or 5 cm below the upper water level in an LBI of the present invention (details explained in Pilot experiment 2a), FIG. 11 is a diagram chart showing the comparative results of embryo development as explained above under FIG. 10, but being immersed to depths of 0, 5, 9 or 13 cm below the upper level of the water in an LBI of the present invention (details explained in Pilot experiment 2b);

FIG. 12 is a bar chart showing the comparative results of embryo development in air-tight flexible laminate foil bags filled with a mixture of either 3.5% or 5% carbon dioxide in air and immersed to the same depth of the water in an LBI of the present invention (details explained in Pilot experiment 3);

FIG. 13 is a bar chart showing the comparative results of embryo development in air-tight flexible laminate foil bags filled with either expiration air or 4% carbon dioxide in air and immersed to the same depth of the water in an LBI of the present invention (details explained in Pilot experiment 4a); and FIG. 14 is a bar chart showing the results of 25 embryo development experiments performed in air-tight flexible laminate foil bags filled with expiration air and immersed to the same depth of the water in an LBI of the present invention (details explained in Pilot experiment 4b).

DETAILED DESCRIPTION OF THE DRAWINGS

FIG. 1 shows a top view of an embodiment of an incubator 10 according to the present invention. 20 indicates vertical side- and endwalls of a box-shaped tank having an open top side, an insulating jacket (not shown) surrounding the tank on its end, side and bottom walls may be provided. The tank is covered by a roof 40 having rectangular openings 50 for four box-shaped vessels to be submerged in a liquid contained in the tank. The vessels have a flange extending horizontally from the upper edge of the vessels to engage with the edges surrounding the openings in the roof so as to support the vessels thereon. 55 indicates an opening in the roof for submerging or immersing racks or baskets containing sealed bags directly in the liquid. Particular means may be provided for lowering these racks and baskets to specific depths from the upper level of the liquid in the incubator tank. 60 Indicates a combined temperature control, heating and circulator means to agitate the liquid in the tank, e.g. a stirrer or a propeller, so as to maintain an essentially constant temperature throughout the bath. 70 indicates a gas regulating unit. The liquid in the tank will preferably be water. When all the vessels are inserted in the openings in the roof of the tank there will be no direct access to the liquid in the tank because all openings in the roof will be covered. Openings 50,55 in the roof not occupied by inserted vessels will be covered with particular lids (not shown).

FIG. 2 is a sectional side view of a box-shaped incubator vessel. 80 indicates the vertical end walls of the vessel and 81 indicates a cover or lid at the top of this vessel. 82 indicates an inlet, e.g. a pipe stub to be connected with a tube or hose and optionally a valve (not shown), for a preheated gas or gas mixture. 83 indicates an outlet, e.g. a pipe stub provided with a valve and optionally connected to a tube or hose, for releasing excess gas from the interior volume of the vessel to the surroundings. 84 indicates an air-tight insulation strip arranged between a flange on the vessel lid 81 and a flange at the top of the vertical vessel walls 80. 85 Indicates a handle for lifting or lowering the lid or the whole vessel. Clamps or screws (not shown) may be provided along the flanges of the lid and the vessel for maintaining a firm air-tight sealing therebetween. 95 indicates the upper level of a water layer placed on the bottom of the vessel for providing maximum humidity inside the vessel.

FIG. 3 is a sectional side view of another box-shaped vessel in the tank of the incubator shown in FIG. 1. 80 indicates the vertical end wall of the vessel and 81 indicates the cover at the top of this vessel. 82 indicates an inlet, e.g. a pipe stub to be connected with a tube or hose and optionally a valve (not shown), for a preheated gas mixture. 90 indicates a rack with shelves 91 placed in the vessel for supporting culture containers, e.g. culture flasks, petri- or well-dishes or flexible, sealed bags. 95 indicates the upper level of a water layer placed on the bottom of the vessel for providing maximum humidity inside the vessel. 100 indicates the upper level of the liquid in the incubator tank.

FIG. 4 is a sectional end view of the vessel shown in FIG. 3. 80,81,82,90,91,95 and 100 have the same meaning as in FIG. 3 and 83 indicates an outlet, e.g. a pipe stub provided with a valve and optionally connected with a tube or hose, for releasing excess gas from the interior of the vessel to the surroundings.

Figure 5:
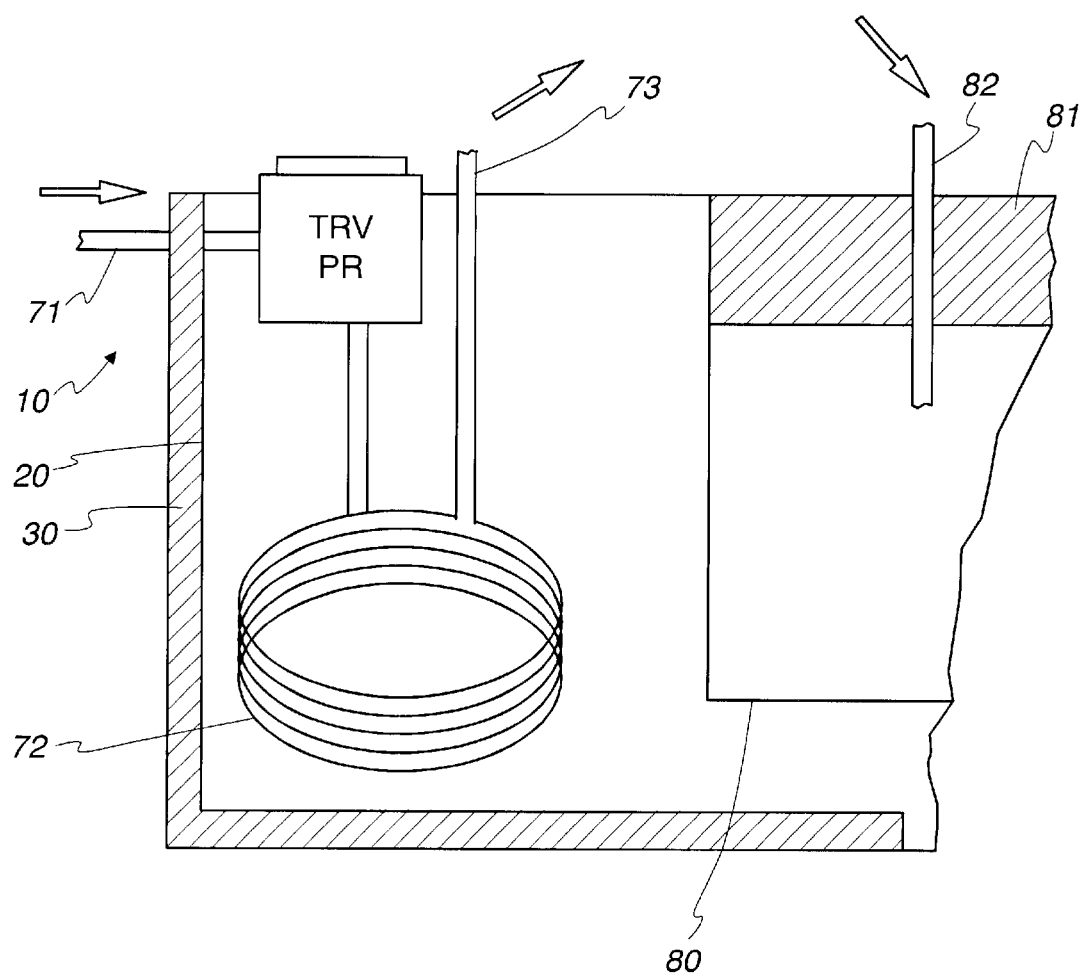
FIG. 5 is a sectional side view in part showing the gas-supplying system for the culture vessels of the incubator shown in FIG. 1.

FIG. 5 is a sectional side view in part of the incubator shown in FIG. 1, which shows the gas-supplying system for the culture vessels submersted in the incubator tank. 10 indicates the entire incubator, 20 the incubator tank, 30 the insulating jacket surrounding the tank, 70 the gas regulating unit comprising a time regulated valve (TRV) and a pressure regulator (PR). 71 indicates a tube supplying gas or a gas mixture from a source therefore (not shown), 72 indicates a tube coil (preferably of a thin-walled metal tube) for preheating the gas or gas mixture to be supplied to the culture vessels 80. 73 indicates the outlet from the tube coil passing preheated gas or gas mixture from the coil to the inlet(s) 82 of the incubator vessels 80. As previous 81 indicates a thermal insulating lid at the top of the incubator vessel.

Figure 6:
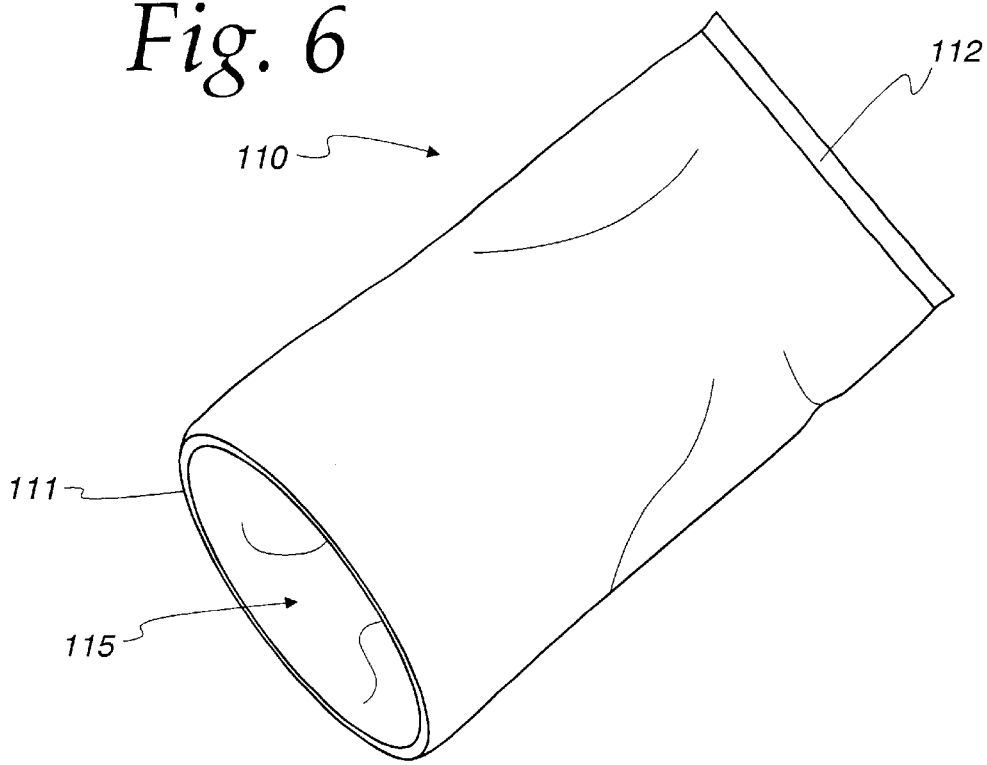
FIG. 6 is a perspective view of an embodiment of a flexible, sealable bag for performing sub- or immersed culture of cells and tissues according to the present invention.

FIG. 6 is a perspective view of an embodiment of a flexible, sealable bag for performing sub- or immersed culturing of cells and tissues according to the present invention. 110 indicates the bag, 112 indicates a heat-sealed stripe across the bottom end of the bag, 115 indicates the opening of the bag at its top end before sealing it, and 111 indicates a heat sealable film binded to the inside of the bag. When the culture medium and the cells to be cultured have been introduced into the bag, either directly or in a receptacle like a petri- or well-dish, an appropriate air mixture will repeatedly (4–5 times) be blown into the bag and expelled by a slight mechanical pressure applied on the outside of the bag to ensure complete exchange of the gas surrounding the culture and the bag will then be hot sealed along a stripe across the bag near its top end 115. The bag will then be ready for submersing or immersing it into the liquid of a liquid incubator.

Figure 7:
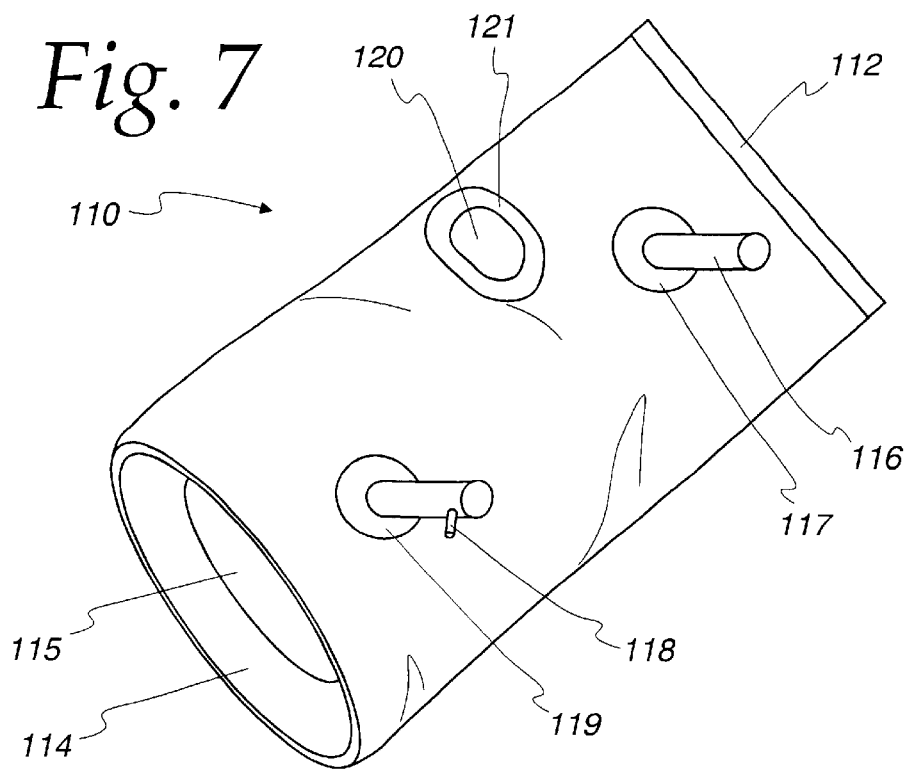
FIG. 7 is a perspective view of another embodiment of a flexible, sealable bag for performing sub- or immersed culture of cells and tissues according to the present invention, said bag being provided with in- and outlet for supplying gas mixture to and releasing excess gas from the bag.
Figure 9:
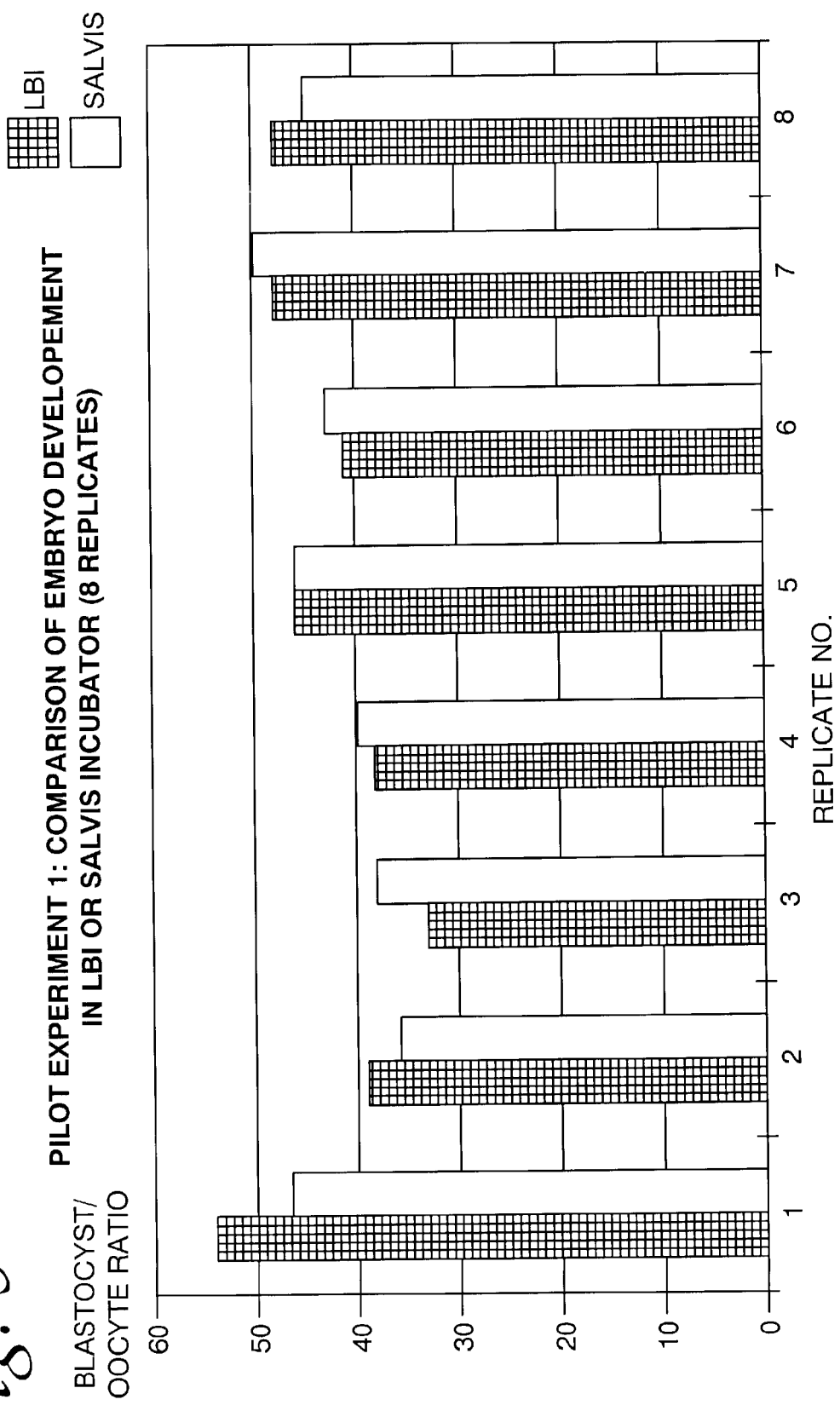
FIG. 9 is a bar chart showing the comparative results of embryo development in a liquid bath incubator (LBI) according to the present invention and in a Salvis® incubator (details explained in Pilot experiment 1)

FIG. 7 is a perspective view of another embodiment of a flexible bag for performing sub- or immersed culturing of cells and tissues according to the present invention. 110, 112 and 115 have the same meaning as explained for FIG. 9. 114 indicates a pressure sensitive adhesive stripe at the inner surface of the bag, which is covered by a slip tape or strip. When sealing the open top end of the bag the slip tape or strip is simply pulled off and the bag is sealed by subjecting the outside surface of the bag at its open end to a firm calendering pressure. 116 indicates an inlet, e.g. in the form of a pipe stub, for introducing a culture gas or gas mixture into the bag after its sealing at its open top end 115. 117 Indicates a ring-shaped sealing stripe fastening the inlet tube to the bag. 118 indicates an outlet for excess gas in the bag, which gas will be released to the surroundings. Also the outlet may be in the form of a pipe stub, and 119 indicates a ring-shaped sealing stripe fastening the outlet 118 to the surface of the bag. When culture medium and cells have been introduced into the bag, optionally in a receptacle like a petri- or well-dish, the bag will be rinsed by blowing the culture gas or gas mixture through the inlet 116 and out through the outlet 118. When the interior of the bag has been thoroughly rinsed in this manner the inlet and outlet will be closed, e.g. by valves (not shown) or clamps (not shown) or by heat-sealing the pipe stubs 116 and 118. The sealed bag is then submerged or immersed in the liquid of a liquid incubator of the present invention.

Instead of the inlet 116 and outlet 118 the bag can be provided with one or more selfsealing membranes 120, e.g. rubber septums, sealed to the wall of the bag with a ring-shaped sealing stripe 121 or optionally with a circular sealing layer provided between the membrane and the wall of the bag. The presealed bag can then be filled with the proper gas mixture through a sterile injection needle passed through the membrane into the interior volume of the bag. When retracting the needle the puncture hole made by the needle will be closed automatically due to the selfsealing membrane material.

Figure 8:
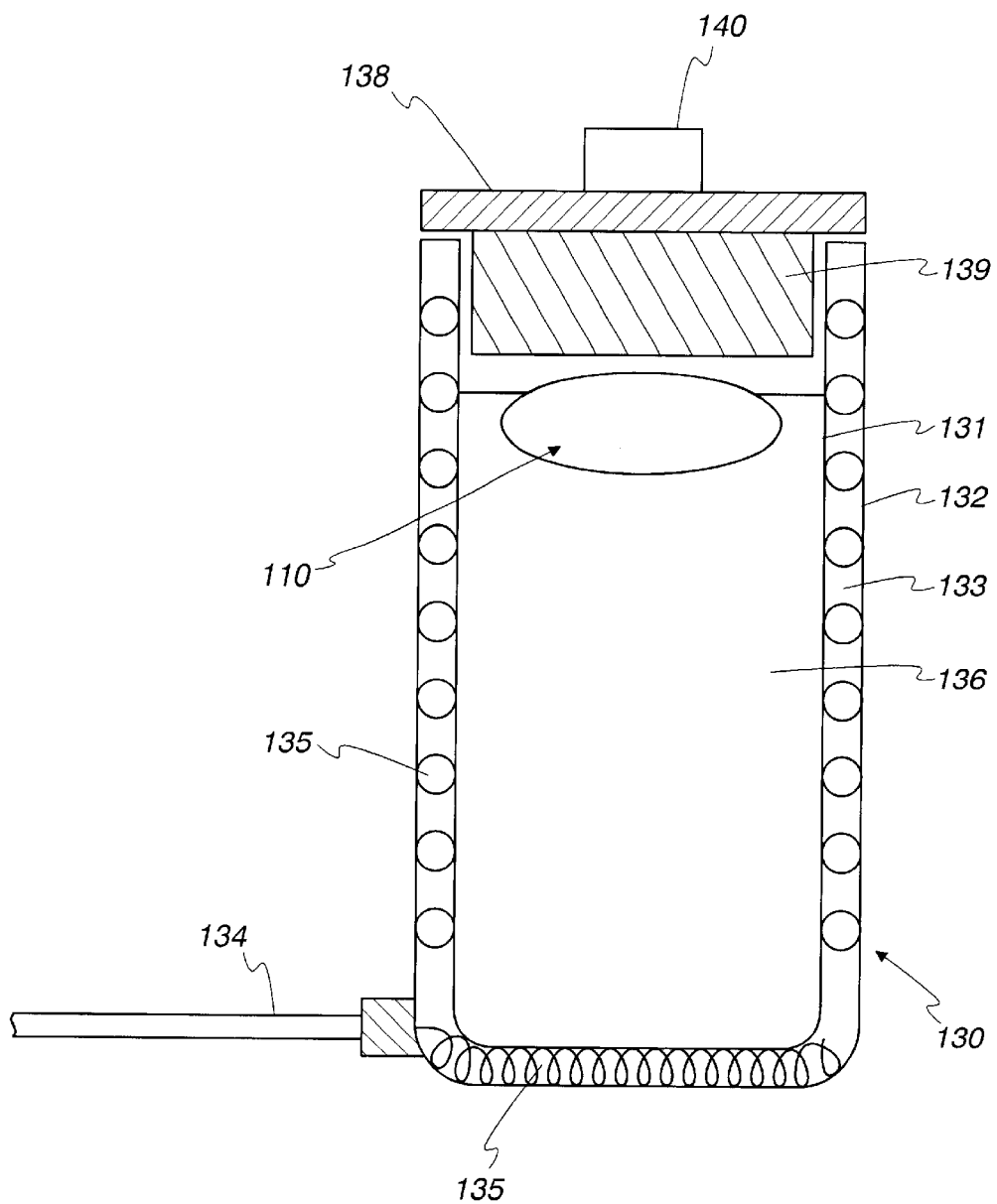
FIG. 8 is a sectional view of a transportable liquid bath incubator for performing culture of cells and tissues in the field.

FIG. 8 is a sectional view of a transportable liquid bath incubator for performing culture of cells and tissues in the field according to the present invention. In principle this incubator consists of a thermos container 130 comprising an inner container 131, an outer container 132 and a heating jacket 133 therebetween, expediently containing a heating medium, e.g. water or another suitable liquid. Electrical heating means 135, e.g. an isolated metal coil or helix is provided in the jacket for heating the jacket medium to a selected temperature controlled by a thermostate sensor (not shown). The electric heating means is supplied with electric power by the electric cable 134 which in turn is connected to an electrical power supply, e.g. a battery, an accumulator or a car cigarette lighter plug (not shown). 136 indicates the incubator liquid, preferably water, and 110 indicates a sealed culture bag immersed in the incubator liquid. 138 indicates a cover plug provided with a thermal insulating lower part 139. 140 indicates a handle for pulling up the cover plug. The cover plug 138,139 may also be provided with threads to be engaged with corresponding threads at the inside (or outside) of the container 130 at its top. In addition to the heating jacket 133 a further insulating jacket comprising an insulating material like glass-wool can be arranged around and enclosing the outer container 132.

In some respects the transportable liquid incubator may resemble a thermos bottle or flask except that it must be provided with heating means and a thermostate controlling means providing for strict control of the temperature of the incubator liquid.

Pilot Experiment 1

Embryo Production

Maturation of bovine oocytes, fertilization and culture of embryos has been described in detail elsewhere (Vajta et al, 1995). Briefly, oocytes were aspirated from slaughterhouse-derived ovaries, matured for 24 h in TCM-199 medium supplemented with 15% calf serum, eCG and hCG. Insemination (Day 0) was performed with frozen-thawed, Percoll-selected sperm. After 22 h, zygotes were vortexed, then cultured on the granulosa cell monolayer formed spontaneously in the maturation dishes in TCM-199 supplemented with 5% (15% from Day 5) calf serum. Cultures were evaluated on Day 7 and 8 after insemination. For maturation and fertilization, which processes require relatively short incubation time, a double-wall K-system box with continuous gas flow and heated by an external circulator (Henning Knudsen Engineering, Hillerød, Denmark) was used. Embryo cultures were performed in the thermostates described below.

Liquid Bath Incubator (LBI) used for Present Experiments

A simple preliminary model of an LBI was constructed and used for the preliminary experiments. A large covered plastic container (W×D×H: 380×310×180 mm) filled with water was heated by a HETO DT circulator placed in the center of the cover. In the corners, four cylindrical shaped plastic boxes (D×H: 115×135 mm) with airtight and thermoinsulated caps were inserted. However, a 30 mm part of the plastic boxes, partially uninsulated, was above the water level. Two plastic tubes with 1 mm inner diameter were fixed through the caps for gas delivery. Opening and closing of these tubes as well as starting and stopping gas flow was performed manually. Approx. 1 m of the plastic gas tube was immersed into the water to achieve preheating of the gas mixture.

Thermostate used for Control Experiments

Four single-wall metal boxes (W×D×H: 160×150×80 mm); (K-system, Henning Knudsen Engineering, Hillerød, Denmark) were placed in a Salvis Thermocenter (Salvis, Luzern, Switzerland) in two vertical lines. Vertical airtight doors were placed on the front wall, and pre-heated humidified gas was delivered continuously to ensure the appropriate environment.

Comparison of Parameters

Approximate volume of suggested metal boxes and used plastic boxes was the same, about 1400 $cm^3$. Filling these boxes with gas mixture required no more than 2 min. at appr. 0.1 bar pressure.

Temperature of the gas reaching the boxes was 31–32° C., which was unsatisfactory. However, using a spiral metal tube instead of plastic tube will ensure better heating of the gas mixture.

The water surrounding the boxes had a constant and even temperature. However, insufficient thermal insulation at the top, and insufficient thermoconductivity at the bottom of the plastic boxes resulted in 0,5–1° C. differences between the temperature of the water outside and the air inside the box (at 39.5° C. water temperature). The magnitude of this difference depended on the room temperature.

Temperature recovery to 0.5° C. below the original level needed 4–10 minutes after a short opening the door, and 12–30 minutes were required for recovery to the original level. Using metal boxes recovery is expected to be much quicker (2–3 minutes and 5–9 minutes, respectively).

In the Salvis Thermocenter, the temperature in the boxes was appr. 0.5° C. below the adjusted level. Recovery rates did not differ from those observed using the plastic boxes and the LBI.

Results of Embryo Culture Experiments

When used for embryo culture, the water temperature of the LBI was adjusted to 39.5° C. In this way the air temperature of the boxes was between 38.5° C. and 39° C. Salvis Thermocenter was adjusted to 39° C. In this way the air temperature of the boxes was about 38.5° C. Results of Pilot experiment 1 are shown in FIG. 9.

Cumulative results achieved in eight replicates were 145 blastocysts/333 oocytes (44%) and 255 blastocysts/567 oocytes (45%) in the LBI and Salvis incubator, respectively.

Conclusion: There was no significant difference between the quantitative results achieved by the two thermostates. The blastocysts ratios achieved were among the highest published so far (Brackett and Zuelke, 1993; Farin et al., 1995; Hernandez-Lendezma et al., 1995). When evaluating the quality of embryos by morphological criteria using stereo microscopy, no differences between the two groups could be revealed. In two cultures of one experiment (code 8), hatching rate was followed until Day 10 and was 100% (22/22) and 91% (21/23) in the WBI and the Salvis group, respectively.

Pilot Experiment 2

Bovine oocytes were collected from slaughterhouse-derived oocytes, matured and fertilized in vitro as described in Pilot experiment 1. After 22 to 32 h cocultivation of gametes (fertilization) embryos were vortexed, then randomly distributed into groups and cultured on the granulosa cell monolayer formed spontaneously in the maturation four-well dishes (Nunc, Denmark) in TCM-199 medium supplemented with 5% (10% from Day 4) calf serum. Cultures were evaluated on Day 8. For maturation and fertilization, K-system incubators were used (see Pilot experiment 1). Embryo cultures were performed in 10×11 cm laminated foil sacks (SFK, laminate foil 3370 UBA, 12 micron PETP Metal/75 micron PE Gold) filled with expiration air, heat-sealed and submerged into a 38.7° C. water bath. The depth of submerging on Day 1 to Day 4 (Day 0=day of insemination) was either 1 cm or 5 cm under the water level in Pilot experiment 2a, and either 1 cm, 5 cm, 9 cm or 13 cm in Pilot experiment 2b. All bags were immersed to 1 cm under the water level in both experiments on Day 4 to Day 8.

Results: As shown in FIG. 10, significant (P<0.05 by Chi-square test) increase of blastocyst/oocyte rates was achieved, when embryos were subjected to 5 centimeter water pressure during the first 4 days of development (Pilot experiment 2a). Cumulative rates of 15 replicates were 329 blastocysts/365 oocytes (49%) and 262 blastocysts/599 oocytes (44%) in 5 and 1 centimeter water pressure, respectively. Further increase of the pressure did not improve developmental rates. However, as shown in FIG. 11, increase of the pressure up to 9 water cm did not impair developmental rates (Pilot experiment 2b).

Conclusion: The results of Pilot experiment 2 have proven, that the slight increase of pressure in the foil bag submerged into water had no detrimental effect on embryos up to the suggested maximum depth (9 centimeter water). In contrast, a slight increase of embryo developmental rates could be achieved by a moderate increase of the pressure on Day 1–Day 4 of embryo culture.

Pilot Experiment 3

Bovine oocytes were collected from slaughterhouse-derived oocytes, matured and fertilized in vitro as described in Pilot experiment 1. After 22 to 32 h cocultivation of gametes (fertilization) embryos were vortexed, then randomly distributed into groups and cultured on the granulosa cell monolayer formed spontaneously in the maturation four-well dishes (Nunc, Denmark) in TCM-199 medium supplemented with 5% (10% from Day 4) calf serum. Cultures were evaluated on Day 8. For maturation and fertilization, K-system incubators were used (see Pilot experiment 1). Embryo cultures were performed in 10×11 cm laminated foil sacks as described in Pilot experiment 2, filled either with a mixture of 3.5% or 5% carbon dioxide in air, heat-sealed and submerged into a 38.70° C. water bath.

Results: As shown in FIG. 12, significant (P<0.05 by Chi-square test) increase of blastocyst/oocyte rates was achieved, when embryos were cultured in 3.5% carbon dioxide. Cumulative rates of 9 replicates were 417 blastocysts/856 oocytes (51%) and 366 blastocysts/856 oocytes (43%) in 3.5% and 5% carbon dioxide in air, respectively.

Conclusion: The results of Pilot experiment 3 have proven, that slight changes in composition of the atmospheric gas mixture may influence the development of bovine pre-implantation embryos. In our culture system, the 3.5% carbon dioxide in air mixture resulted in significant increase in the developmental rates. The foil bag system was a simple and useful tool in which these investigations could be performed.

Pilot Experiment 4

Bovine oocytes were collected from slaughterhouse-derived oocytes, matured and fertilized in vitro as described in Pilot experiment 1. After 22 to 32 h cocultivation of gametes (fertilization) embryos were vortexed, and cultured on the granulosa cell monolayer formed spontaneously in the maturation four-well dishes (Nunc, Denmark) in TCM-199 medium supplemented with 5% (10% from Day 4) calf serum. Cultures were evaluated on Day 8. For maturation and fertilization, K-system incubators were used (see Pilot experiment 1). Embryo cultures were performed in 10×11 cm laminated foil sacks as described in Pilot experiment 2, filled either with a mixture of 4% carbon dioxide in air (Pilot experiment 4a) or with expiration air from one person (Pilot experiment 4b), were heat-sealed and submerged into a 38.70° C. water bath.

Results: As shown in FIG. 13, no significant (P>0.1 by Chi-square test) difference of the developmental rates of the two groups in Pilot experiment 4a was observed. Cumulative rates of 6 replicates were 136 blastocysts/294 oocytes (46%) and 134 blastocysts/285 oocytes (47%) in 4% carbon dioxide in air and expiration air, respectively. In FIG. 14, results of 25 embryo culture experiments (Pilot experiment 4b) are summarized. The cumulative developmental rate was 517 blastocysts/1052 oocytes (49%).

Conclusion: The results of Pilot experiment 4a and 4b have proven, that expiration air is suitable to replace the industrial gas mixture, and in a large series of experiments, high and even embryo developmental rates can be achieved by the simplest way of production of the atmospheric gas for embryo cultures. To use expiration air for embryo culture, the foil bag system was uniquely suitable, as the filling was easy and the required volume was low.

Pilot Experiment 5

Bovine oocytes were collected from slaughterhouse-derived oocytes, matured and fertilized in vitro as described in Pilot experiment 1. After 30 to 32 h cocultivation of gametes (fertilization) embryos were vortexed, and cultured on the granulosa cell monolayer formed spontaneously in the maturation four-well dishes (Nunc, Denmark). Before use, the outer frame of the dishes was cut, and the remaining 4.5×4.5×1 cm dish was used for the experiments. Embryos were cultured in TCM-199 medium supplemented with 5% calf serum. Cultures were evaluated on Day 7. For maturation and fertilization, K-system incubators were used (see Pilot experiment 1). Embryo cultures were performed in 6.5×7 cm laminated foil sacks filled with expiration air, heat sealed and submerged into a Minitübe transportable incubator (Minitübe GMBH, 8311 Tiefenbach, Germany; Ref. no. 19180/0000) sealed previously to become waterproof, then filled with water.

Results: Blastocyst/oocyte rates of three identical replicates were 20/44 (45%), 16/43 (37%), and 22/52 (42%), respectively. Cumulative developmental rate of the three replicates was 58/139 (42%).

Conclusion: The results of Pilot experiment 5 have proven, that the foil-bag system combined with the use of expiration air is suitable to establish suitable culture conditions at on field situations for as highly sensitive objects as in vitro fertilized bovine embryos. This culture can be maintained for 7 days and results in good developmental rates. So far, no tissue culture equipment fulfilling these requirements has been available.

Pilot Experiment 6

Bovine oocytes were collected from slaughterhouse-derived oocytes, matured and fertilized in vitro as described in Pilot experiment 1. After 30 to 32 h cocultivation of gametes (fertilization) embryos were vortexed, and cultured on the granulosa cell monolayer formed spontaneously in the maturation four-well dishes (Nunc, Denmark). Embryos were cultured in TCM-199 medium supplemented with 5% calf serum. Cultures were evaluated on Day 8. For maturation and fertilization, K-system incubators were used (see Pilot experiment 1). Embryo cultures were performed in 10×11 cm transparent laminated foil sacks (Rexam Metallising, Camclear Polyester Laminate 12/45, Anti-Fog). The inner surface of the foil was moistened by sterile paraffin oil, and the foil was kept attached to the bottom of the dish, to increase optical clarity. Sacs were filled with expiration air, then sealed. In Pilot experiment 6a, foil sacs were immersed into a 38.6° C. water bath, but during the 7 days of the culture, 5 times taken out of the water bath, placed on heated stage of an inverted microscope, observed and photographed (each investigation was performed in less than 5 min). In Pilot experiment 6b, the transparent foil bag was wrapped again in laminated foil described in Pilot experiment 2, then placed on the heated stage of an inverted microscope, covered with a transparent plastic box (16× 16×4 cm, without bottom sheet) and cultured for nine days.

Results: Blastocyst/oocyte rates of four identical replicates in Pilot experiment 6a were 20/39 (51%), 18/46 (39%), 18/41 (44%), 24/52 (46%), respectively. Cumulative developmental rate of the four replicates was 45%. In Pilot experiment 6b, embryos cultured in double sacks on the microscope stage reached the blastocysts/hatched blastocysts stage without remarkable morphological alterations.

Conclusion: The transparent foil has been proven suitable for maintaining the atmospheric conditions of the culture and for visualization of the embryos under inverted microscope. In Pilot experiment 6a, the repeated investigations did not result in severe impairment in the development of bovine preimplantation embryos. In Pilot experiment 6b, a continuous on stage microscopic investigation of the development of embryos from one cell stage till the hatched blastocyst stage was possible. Thus, the foil bag system has been proven to be a simple, inexpensive and efficient tool for repeated or continuous investigation of bovine embryo development.

Conclusion

The suggested Liquid Bath Incubator is a basically new solution for culturing sensitive cells and tissues. So far known, this type of incubator is not included in the production list of major incubator-producing companies (Heraeus, New Brunswick, Heto, Jouan, Forma Scientific etc.) and no scientific publication deals with this idea. LBI offers the following advantages:

1. Temperature stability, quick recovery after opening, no possibility of overheating.
2. Gas mixture stability, quick recovery after opening.
3. Humidity stability.
4. Flexibility in using different gas mixtures
5. Flexibility in using different atmospheric pressure
6. Safety of operation: the only source of trouble is the circulator, which is generally regarded as one of the most trouble-free laboratory equipments.
7. Cost-efficiency price
8. Economy at work: very few gas mixture is needed, maintenance costs and work are minimal
9. Less danger of contamination, less problem with cleaning.
10. Transportability
11. On-field establishment of tissue culture environment
12. Possibility for frequent or continuous microscopic observation.

In conclusion, the theoretical background and the comparative characterization of the suggested incubation system can be summarized in the following two tables:

| Cells and tissues require during development | Provided media | in vitro by incubator |
|---|---|---|
| water, salts, nutrients, amino acids, hormones, growth factors | + | |
| defined pH ($CO_2$/bicarbonate buffer system) | + | + |
| defined $O_2$ | | + |
| constant temperature | | + |

| Characteristics of an ideal IVF incubator | Commercially available | Suggested LBI |
|---|---|---|
| constant temperature | + | ++ |
| constant gas phases ($CO_2$, $O_2$) | + | ++ |
| high speed of recovery of parameters | + | +++ |
| reliability | + | +++ |
| flexibility | + | +++ |
| cost-efficiency (purchase, function) | + | +++ |
| easy operation | ++ | + |
| easy cleaning, sterility | + | ++ |
| transportability | − | ++ |
| on-field establishment of cultures | − | ++ |
| microscopic follow-up | + | +++ |

REFERENCES

Avery B, Greve T. Impact of incubator type on the yield of in vitro produced bovine blastocysts. Acta vet. scand. 1992; 33: 341–348.

Boone W R, Saphiro S S. Quality control in the in vitro fertilization laboratory. Theriogenology 1990; 33: 23–50.

Brackett B G, Zuelke K A. Analysis of factors involved in the in vitro production of bovine embryos. Theriogenology 1993; 39: 43–64.

Farin C E, Hasler J F, Martus N S.: "Comparison of Menezo B2 and TCM 199 media for in vitro production of bovine blastocysts". Theriogenology 1995; 43: 210.

Gordon I.: "Laboratory production of cattle embryos". Biotechnology in Agriculture No. 11. CAB International, Wallingford, UK, 1994; 250. pp.

Hernandez-Lendezma J J, Villanueva C, Sikes J D, Roberts R M.: "Comparison of co-culture and conditioned medium on expansion and hatching of in vitro derived bovine blastocysts". Theriogenology 1995; 43: 233.

Vajta G, Holm P, Callesen H, Greve T.: "Overall efficiency of in vitro embryo production and vitrification in cattle". Theriogenology 1996; 45: 683–689.

Vajta G.: "Practical application of IVF in cattle". Thesis for the "Doctor of Science" degree submitted to the Hungarian Academy of Science, 1994.

Chesne O. Heyman Y, Peynot N, Renard JP: "Nuclear transfer in cattle; birth of cloned calves and estimations of blastomere totipotency in morulae used as a source of nuclei. "C.R. Acad. Sci. Paris, Life Science, 316: 481–491, 1993.

Fukui Y, McGowan L T, James R W, Pugh P A, Tervit H R: "Factors affecting the in-vitro development to blastocysts of bovine oocytes matured and fertilized in-vitro". J. Reprod. Fertil. 92: 125–131, 1991.

What is claimed is:

1. A method of culturing sensitive cells or tissues selected from oocytes and embryos derived from multicellular organisms comprising immersing or submerging sealed bags comprising culture medium, a gaseous atmosphere and the cells or tissues to be cultured into a liquid in a thermostatically controlled liquid bath whereby said sealed bags are immersed or submerged into said liquid bath by a holding means, wherein the culture of the cells and/or tissues is effected in receptacles selected from culture flasks, petri dishes or well-dishes within said sealed bags, and wherein said bags are gas and liquid impermeable and flexible.

2. A method according to claim 1, wherein the sensitive cells or tissues are oocytes, fertilized oocytes and preimplantation embryos.

3. A method according to claim 1 wherein the gaseous atmosphere comprises carbon dioxide, oxygen and humidity in appropriate proportions and levels.

4. A method according to claim 1 wherein the gaseous atmosphere is a preheated humidified gas or gas mixture.

5. A method according to claim 1 wherein the composition of the gaseous atmosphere contained in the sealed bag is changed during the culturing.

6. A method according to claim 1 wherein the gaseous atmosphere in the sealed bag during at least a part of the culturing is expiration air.

7. A method according to claim 1 wherein the thermostatically controlled liquid bath is a transportable thermos flask provided with heating means and temperature controlling means.

8. The method of claim 1 wherein said tank has a plug or lid which may contact the flexible, sealed bag containing a gaseous atmosphere for holding the flexible, sealed bag under the surface of the thermostatically controlled liquid bath.

9. A method according to claim 1 wherein the culturing is initially in a first liquid bath at a first temperature and subsequently at a second different temperature which is effected by transferring the sealed bags comprising the sensitive cells and/or tissues to a second liquid bath at said second temperature.

10. A method according to claim 1 wherein the culturing is at a first temperature in said bath and subsequently at a second temperature in said bath which is effected by adjusting said first temperature to said second temperature.

11. A method according to claim 1 wherein the cells and/or tissues are cultured under limited over pressure of up to 9 cm water during at least a part of the culturing.

12. A method according to claim 1 wherein culturing is effected under optimal gas and temperature conditions.

13. A method according to claim 1 further comprising a container, wherein said container is within said bag and wherein said receptacle is within said container.

14. A method of culturing sensitive cells or tissues selected from oocytes and embryos derived from multicellular organisms comprising immersing or submerging sealed bags comprising culture medium, a gaseous atmosphere and the cells or tissues to be cultured into a liquid in a thermostatically controlled liquid bath whereby said sealed bags are immersed or submerged into said liquid bath by a holding means, wherein the culture of the cells and/or tissues is effected in receptacles selected from culture flasks, petri dishes or well-dishes within said sealed bags, wherein said bags are gas and liquid impermeable and flexible, and wherein said culturing is effected under optimal gas and temperature conditions.

* * * * *